United States Patent [19]

Nestor

[11] Patent Number: 4,762,821

[45] Date of Patent: Aug. 9, 1988

[54] N',N''-DIALKYLGUANIDINO DIPEPTIDES

[75] Inventor: John J. Nestor, San Jose, Calif.

[73] Assignee: Syntex (U.S.A.) Inc., Palo Alto, Calif.

[21] Appl. No.: 905,828

[22] Filed: Sep. 10, 1986

Related U.S. Application Data

[63] Continuation-in-part of Ser. No. 714,767, Mar. 22, 1985, abandoned.

[30] Foreign Application Priority Data

Mar. 19, 1986 [CN] China .................................. 86101850

[51] Int. Cl.$^4$ ........................ A61K 37/43; C07K 5/06; C07D 207/00; C07D 211/06; C07D 211/60

[52] U.S. Cl. ..................................... 514/19; 530/331; 548/533; 548/538; 546/226; 546/245; 540/609; 540/483

[58] Field of Search ................... 514/19; 530/331; 548/593, 533, 538; 546/226, 245; 540/609, 483

[56] References Cited

U.S. PATENT DOCUMENTS

| | | | |
|---|---|---|---|
| 4,046,889 | 9/1977 | Ondetti et al. | 424/244 |
| 4,374,829 | 2/1983 | Harris et al. | 514/19 |
| 4,470,972 | 9/1984 | Gold et al. | 424/177 |
| 4,472,380 | 9/1984 | Harris et al. | 424/177 |
| 4,500,518 | 2/1985 | Gordon et al. | 514/2 |
| 4,587,258 | 5/1986 | Gold et al. | 514/412 |

FOREIGN PATENT DOCUMENTS

| | | | |
|---|---|---|---|
| 12401 | 6/1980 | European Pat. Off. | |
| 0050800 | 5/1982 | European Pat. Off. | 514/19 |
| 65301 | 11/1982 | European Pat. Off. | |
| 79522 | 5/1983 | European Pat. Off. | 514/19 |
| 79022 | 5/1983 | European Pat. Off. | |

OTHER PUBLICATIONS

U.S. Patent Application Ser. No. 06/905,827, filed 9/10/86, (Arzeno et al).

J. J. Nestor, Jr., et al., "Peptides-Structure and Function", *Proc. Eighth Ames. Peptide Symposium*, V. J. Hruby et al., Eds., Pierce Chem. Co., Rockford, IL, 1984, pp. 861–864.

*Primary Examiner*—Delbert R. Phillips
*Attorney, Agent, or Firm*—Derek P. Freyberg

[57] ABSTRACT

N',N''-dialkylguanidino dipeptides with angiotension converting enzyme (ACE) inhibiting activity are useful as antihypertensives. Proline and proline analogs are components of the dipeptides.

19 Claims, No Drawings

N',N'''-DIALKYLGUANIDINO DIPEPTIDES

CROSS-REFERENCE TO RELATED APPLICATION

This application is a continuation-in-part of my co-pending application Ser. No. 06/714,767, filed Mar. 22, 1985, now abandoned, entitled "$N^G,N^{G'}$-Dialkylguanidino Dipeptide Derivatives", which is incorporated herein by reference.

BACKGROUND OF THE INVENTION

1. Field of the Invention

This invention relates to N',N'''-dialkylguanidino dipeptide derivatives and the pharmaceutical uses thereof. In particular this invention relates to the use of N',N'''-dialkylguanidino dipeptide derivatives as angiotensin converting enzyme (ACE) inhibitors and antihypertensives.

BACKGROUND TO THE INVENTION

Blood pressure can be lowered by angiotensin converting enzyme inhibitors. Examples of such drugs are described in European Patent Applications Nos. 12401, 65301 and 79022 and in *Chem. Abstracts* 9525634j (1981) and U.S. Pat. No. 4,046,889 to Ondetti, et al.

McGregor et al., *J. Cardiovasc. Pharmacol.*, 7 (Supp. 1) 1985, p. 582, discuss the effect of ACE inhibitors in combination with conventional anti-hypertensives, including the calcium entry blocker nifedipine. Brunner et al., *J. Cardiovasc. Pharmacol.*, 7 (Supp. 1) 1985, p. 52, discuss the potency of a variety of ACE inhibitors.

SUMMARY OF THE INVENTION

The ACE inhibitors of the present invention are dipeptides containing α-amino acids having an N',N'''-dialkylguanidino functionality.

The following numbers (1 to 14) refer to the compounds of the invention which are organized in groups 1 to 14 below:

1. This invention provides a compound of the general Formula (A)

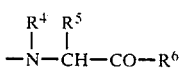

wherein $R^1$ represents hydroxy, lower alkoxy, benzyloxy or amino optionally substituted with one or two lower alkyl groups;

each of $R^2$ and $R^3$ represent (1) hydrogen or, preferably, lower alkyl (optionally omega-substituted with phenyl or naphthyl, less preferably omega-substituted with di(lower alkyl)guanidino), or

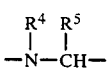

i.e. an N',N'''—di(substituted)quanidinoalkyl [$N^G,N^{G'}$—di(substituted)guanidinoalkyl], one of $R^2$ and $R^3$ being (1), the other being (2);

the group

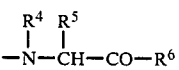

is an amino acid residue selected from the group of imino acid residues, preferably cyclic imino acid residues in which the subgroup

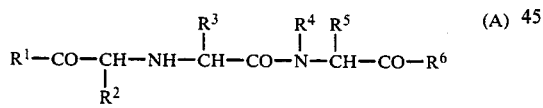

forms a heterocyclic radical containing one nitrogen atom and up to 9 ring carbon atoms, in particular said cyclic imino acid residue is or is derived from proline, hydroxyproline or proline analogs;

$R^6$ is hydroxy, lower alkoxy, benzyloxy or amino optionally substituted with one or two lower alkyl groups;

$R^7$ and $R^8$ are independently lower alkyl optionally substituted on other than the α-carbon atom with 1 to 5 fluorine atoms; and n is an integer from 3 to 5, preferably 4; and their pharmaceutically acceptable, non-toxic salts.

2. Preferred are compounds of Formula (A) wherein one of $R^2$ and $R^3$ is lower alkyl, benzyl or 2-phenylethyl.

3. Even more preferred compounds are those wherein one of $R^2$ and $R^3$ is lower alkyl or 2-phenylethyl, and the group

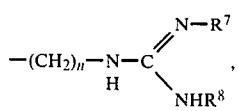

represents a proline radical (I), a proline analog radical in which the pyrrolidine ring is substituted by an oxo group (IV), or by hydroxy, mercapto, (lower alkyl)thio or lower alkoxy (V), or the proline radical function is replaced with the residues II, III or VI:

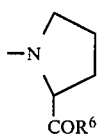
(I)

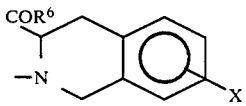
(II)

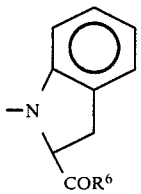
(III)

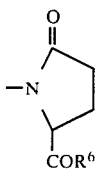
(IV)

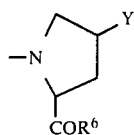
(V)

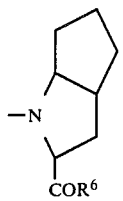
(VI)

(in which X is hydrogen, nitro, lower alkyl, chloro or bromo), and $R^6$ is hydroxy or benzyloxy.

4. Preferred subgroups of the groups 1 to 3 include the compounds wherein $R^2$ is the dialkylguanidino substituted radical (2).

5. Another preferred subgroup of the groups 1 to 3 includes the compounds wherein $R^2$ is 2-phenylethyl.

6. A subgroup of the groups 1 to 4 includes the compounds wherein $R^3$ is lower alkyl with 1 to 4 carbons.

7. A preferred subgroup of group 6 includes the compounds wherein $R^3$ is methyl, ethyl, or n-propyl. 8. In a further preferred subgroup of the groups 1 to 7 the group

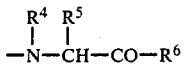

forms a proline residue.

9. Particularly preferred are the compounds wherein the group

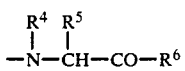

is a proline residue or is selected from the groups II, III or VI and $R^6$ is hydroxy.

10. An important subgroup of the groups 1 to 7 or 9 includes the compounds wherein the proline residue is replaced with II.

11. The most preferred subgroup of group 10 includes the compounds wherein X is hydrogen.

12. It is further preferred that in all the groups of compounds $R^7$ and $R^8$ are lower alkyl with 1 to 4 carbon atoms.

13. A particularly preferred subgroup of group 12 includes the compounds with $R^7$ and $R^8$ being methyl, ethyl, 2,2,2-trifluoroethyl, n-propyl, or n-butyl.

14. The most preferred subgroup of group 13 includes the compounds with $R^7$ and $R^8$ being ethyl.

This invention further provides a pharmaceutical composition which comprises a pharmaceutically effective amount of a compound of one of the preceding groups and a pharmaceutically acceptable excipient. This pharmaceutical composition is particularly useful for the treatment of hypertension. It is preferred that the pharmaceutical composition include diuretics, or other antihypertensives, for example calcium blockers, particularly nicardipine.

This invention further provides a method of treating hypertension in mammals which method comprises administering a therapeutically effective amount of a compound of Formula (A) or a pharmaceutical composition containing a compound of Formula (A).

This invention further provides for the use of a compound of Formula (A) for the preparation of pharmaceutical compositions. It is preferred that the use of a compound of Formula (A) is for the treatment of hypertension.

This invention further provides a method of preparing pharmaceutical compositions of a compound of Formula (A) wherein the compound is combined with a pharmaceutically acceptable excipient to form pharmaceutical compositions.

The invention further provides a process for the preparation of the compounds of formula (A) described below.

This invention further provides a method for preparing a pharmaceutical composition comprising a dipeptide of Formula (I) or its pharmaceutically acceptable salt and a pharmaceutically acceptable excipient, said method comprising converting said dipeptide or said salt (obtained according to the chemical process described below) and said excipient into said pharmaceutical composition.

DETAILED DESCRIPTION OF THE INVENTION

Definitions

Unless defined otherwise, as used herein the term "lower alkyl" means a branched or unbranched saturated hydrocarbon chain containing one to six carbon atoms. Examples include such as methyl, ethyl, propyl, tert-butyl, n-pentyl, n-hexyl and the like.

As used herein the term "fluoroalkyl" means a branched or unbranched saturated alkyl chain which is substituted with one or more (up to five) fluorine atoms on carbon atoms other than the α-carbon atom. Examples include 2,2,2-trifluoroethyl, 2,2,3,3,3-pentafluoropropyl, and the like.

As used herein the term "lower alkoxy" means the group -OR wherein R is lower alkyl as defined above. Examples include such as methoxy, ethoxy, propoxy, tert-butoxy, n-hexyloxy and the like.

As used herein the term "optional" or "optionally" means that the subsequently described event or circumstance may or may not occur, and that the description includes instances where said event or circumstance occurs and instances in which it does not.

As used herein the term "lower alkyl optionally omega-substituted" means a lower alkyl group as previously defined having an optionally substituted group at the carbon atom furthest from the point of attachment to the remainder of Formula (A).

As used herein the term "aryl" means an optionally substituted aromatic radical containing 6 to 12 ring carbon atoms, particularly optionally substituted phenyl or naphthyl.

As used herein the term "optionally substituted phenyl" means a phenyl, which may or may not be substituted as indicated above, with one to three substituents selected from the group consisting of halo, lower alkyl, or lower alkoxy, both having from one to four carbon atoms, hydroxy, and trifluoromethyl.

As used herein the term "pharmaceutically acceptable salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of formula A also form salts with inorganic bases such as sodium hydroxide, potassium hydroxide, calcium hydroxide, aluminum trihydroxide, magnesium hydroxide or with organic bases such as isopropylamine, trimethylamine, diethylamine, ethanolamine, 2-dimethylaminoethanol or tromethamine.

As used herein the term "acid derivative" includes but is not limited to esters (lower alkyl, benzyl or silyl), amides, acid chlorides, hydroxamic acids and the like.

As used herein the term "proline analog" refers to the heterocyclic compounds from which the above-described residues II to VI are derived.

As used herein the term "sulfonyloxy" refers to (lower alkyl)sulfonyloxy, e.g. methanesulfonyloxy, (halogenated lower alkyl)sulfonyloxy, e.g. trifluoromethanesulfonyloxy, or to (6–12C)arylsulfonyloxy, e.g. p-toluenesulfonyloxy groups.

Unless defined otherwise the formula $R^{1*} \ldots R^{6*}$ denotes a starting material for the compounds of formula A which already contains the dipeptide chain of the compounds of formula A but wherein at least one of $R^{1*}$ and $R^{6*}$ is to be converted to $R^1$ and $R^6$, respectively.

The compounds of this invention have an alkyl substituted guanidine functionality for one of the amino acid residues, $R^2$ or $R^3$. Arginine, a naturally occurring amino acid, has an unsubstituted guanidine functionality. In those compounds of this invention having an arginine derivative as a component (the compounds of Formula (I) with n being 3), both terminal nitrogens on the guanidino functionality of the arginine are substituted with an alkyl functionality. Examples include $N^G,N^{G'}$-dimethylarginine, $N^G,N^{G'}$-diethylarginine, $N^G,N^{G'}$-bis(2,2,2-trifluoroethyl)arginine, $N^G$-methyl-$N^{G'}$-ethylarginine, and the like. Similar compounds of groups 1 to 14 (above) are formed from other alkyl guanidino-substituted amino acids, for example $N^G,N^{G'}$-dimethylhomoarginine, $N^G,N^{G'}$-diethylhomoarginine, $N^G,N^{G'}$-bis(2,2,2-trifluoroethyl)homoarginine, $N^G$-methyl-$N^{G'}$-ethyl-homoarginine, and the like (the compounds of Formula (I) with n being 4).

The alkyl groups make the guanidino functionality more lipophilic and strongly basic, and therefore more able to interact more strongly with cellular membranes.

Certain compounds of this invention include the proline analogs II, III and VI. These proline analogs include 3-carboxy-1,2,3,4-tetrahydro-isoquinoline (THIQ), 2-carboxy-2,3-dihydroindole, 4,5-(trimethylene)proline (3-carboxy-2-azabicyclo[3.3.0]octane), and the like. The hydrocarbon group attached to the proline makes these proline analogs more lipophilic than proline. Such a proline analog is therefore more able to interact more strongly with cellular membranes than non-substituted proline.

The compounds of this invention containing proline analogs II, III and VI are bound more tightly to the cell membranes because of the combined effects of the alkyl substituted guanidine functionality and the hydrocarbon group of the proline analog. This causes a depoting of the compound in the body and places the proline analog containing compounds of the invention nearer to the presumed site of action for a longer time than similar compounds without these features, resulting in a more potent and longer acting pharmaceutical effect.

The compounds of this invention form salts with inorganic and organic acids and bases. These salts are also within the scope of this invention. Such salts include ammonium salts, alkali metal salts like sodium and potassium salts, alkaline earth metal salts like calcium and magnesium salts, salts with organic bases, for example, dicyclohexylamino salts, n-methyl-d-glucamine salts, salts with amino acids like arginine and the like. Also salts may be prepared with organic and inorganic acids, for example, HCl, HBr, $H_2SO_4$, $H_3PO_4$, methanesulfonic, toluenesulfonic, maleic, and fumaric acids, and the like. The non-toxic physiologically acceptable salts are preferred although other salts are useful, for example, in isolating or purifying the product.

As described in more detail below the salts may be formed by conventional means as by reacting the free acid or free base forms of the product with one or more equivalents of the appropriate base or acid in a solvent or medium in which the salt is insoluble, or in a solvent such as water which is then removed under vacuum or by freeze-drying or by exchanging the cations of an existing salt for another cation on a suitable ion exchange resin.

Utility and Method of Administration

The compounds of this invention are ACE inhibitors and thus block the conversion of the decapeptide angiotensin I to angiotensin II, a highly potent pressor substance. Thus, ACE inhibitors can lower blood pressure by inhibiting the biosynthesis of angiotensin II, especially in animals and humans whose hypertension is angiotensin II related. Furthermore, ACE degrades the vasodilating substance bradykinin. Therefore, ACE inhibitors may lower blood pressure by potentiating bradykinin's effects, as well as by inhibiting angiotensin II. Although the relative importance of these and other possible mechanisms remains to be established, ACE inhibitors are known to be effective antihypertensive agents in a variety of animal models and are useful clinically, for example, in many human patients with malignant renovascular and essential hypertension.

A number of in vitro and in vivo models are available to assess the biological activity of ACE inhibitors. (cf E. W. Petrillo, Jr. and M. A. Ondetti, *Medical Res. Rev.* 2, 1 (1982) and references therein). A particularly useful in vitro test employs a preparation of ACE from rabbit lung (either crude or purified) and uses the synthetic substrate (hippuryl-histidyl-leucine) as substrate (D. W. Cushman and H. S. Cheung, *Biochem. Pharmacol.*, 20, 1637 (1971)). The substances to be tested are assessed for their ability to block the cleavage of the substrate and doses which cause 50% inhibition of the hydrolysis of the substrate are determined ($ID_{50}$). In this and other studies, the incorporation of a literature standard (usually captopril) is helpful.

A useful in vivo model used the normotensive rat which is challenged with doses of angiotensin I. Administration of the test drug, either I.V. or by the oral route (p.o.) results in a dose related suppression of the hypertensive response to the angiotensin I challenge (D. M. Gross, et al., *J. Pharmacol. Exp. Ther.*, 216, 552 (1981). Another in vivo model uses the spontaneously hypertensive rat.

The compounds disclosed herein have proven to be potent and long-acting ACE inhibitors both in vitro and in vivo.

Thus, the compounds of this invention are useful as antihypertensives in treating hypertensive mammals, including humans. They can be used to reduce blood pressure in standard pharmaceutical compositions such as tablets, capsules, elixirs for oral administration or in sterile solutions or suspensions. The specific dosing regime will depend on a number of factors such as the individual's weight, severity of the disease, and the like.

The compounds of this invention may be given in combination with other diuretics or antihypertensives. Typically, these are combinations whose individual daily dosages range from one-fifth of the minimally recommended clinical dosages to the maximum recommended levels for the entities when they are given singly. To illustrate these combinations, one of the antihypertensives of this invention is effective clinically in the range 1–200 mg per day and can be effectively combined at levels ranging from 1–200 mg per day with the following diuretics and antihypertensives in dose ranges per day as indicated: hydrochlorothiazide (15–200 mg), chlorothiazide (125–200 mg), ethacrynic acid (15–200 mg), amiloride (5–200 mg), furosemide (5–80 mg) propanolol (20–480 mg), timolol (5–50 mg), methyldopa (65–2000 mg), and nicardipine (5–20 mg). In addition, triple drug combinations such as but not limited to that of hydrochlorothiazide (15–200 mg) plus amiloride (5–20 mg) plus the ACE inhibitor of this invention (1–200 mg) are effective combinations to control blood pressure in hypertensive patients. The above dose ranges will be adjusted on a unit basis as necessary to permit divided daily dosage. Also, the dose will vary depending on the severity of the disease, the weight of the patient and other factors which a person skilled in the art will recognize.

The compounds of Formula (A) have been shown in standard laboratory tests to be ACE inhibitors. Accordingly, the compounds of Formula (A) or their salts or pharmaceutical compositions containing them, may be used in inhibiting the production of angiotensin II, thereby preventing, or controlling hypertension.

Administration of the active compounds of Formula (A) and salts described herein can be via any of the accepted modes of administration for ACE inhibitors. These methods include oral, parenteral and otherwise systemic.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula (A) or the pharmaceutically acceptable salts thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of Formula (A), either oral or intravenous administration is preferred depending on the nature of the disorder being treated.

For oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such compositions may contain 1%–95% active ingredient, preferably 25–70%.

The minimum effective oral dose for spontaneously hypertensive rats of the compounds of this invention is from about 0.01 to 10 mg/Kg body weight. The precise dosage depends on the species receiving the dosage, the severity of the disease state, the manner of administration, the judgment of the prescribing physician and other factors well known in the art. In humans, a minimum effective oral dosage for a 70 Kg human would be between in the range of about 1 mg and 700 mg. No toxic effects have been observed in orally administered dosages in spontaneously hypertensive rats in excess of ten times the minimum effective oral dosage.

Preparation of the Compounds

The compounds of formula A can be produced by a variety of methods known in oligopeptide synthesis. The synthetic approaches are apparent from the numbered dotted lines (1 to 16) in formula A below and the substructure below the formula which depicts the substituents $R^2$ and $R^3$ with more specificity. The dotted lines point schematically to the respective reaction sites and the ensuing table gives a brief description of the various chemical methods that will be described in more detail below. The last column of the table and the letter symbols in parentheses refer to the respective step in the description and in the process claim(s)

-continued

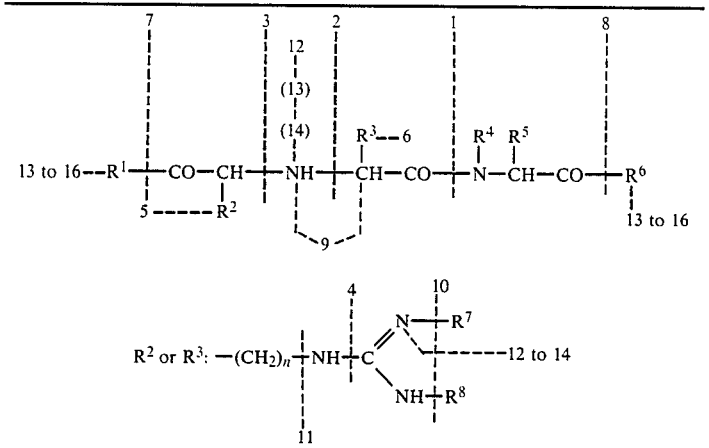

| Approach | Method | Step |
|---|---|---|
| 1 | Condensation (Coupling) | (i) |
| 2 | Condensation (reductive) | (f) |
|  | Alkylation | (n) |
| 3 | Condensation (reductive) | (h) |
|  | Alkylation | (m) |
| 4 | Alkylation | (j) |
| 5, 6 | Oxo reduction | (c) |
| 7, 8 | Hydrolysis | (a) |
|  | Hydrogenolysis | (b) |
|  | Esterification | (k) |
|  | Salt Formation | (d) |
| 9 | Reduction | (g) |
| 10 | Alkylation | (l) |
| 11 | Alkylation | (o) |
| 12 | Acid addition salt formation | (e) |
| 13 | Base salt and free peptide formation | (p) |
| 14 | Acid addition salt and free peptide formation | (q) |
| 15 | Salt conversion | (r) |
| 16 | Amide formation | (s) |

Basically the synthesis proceeds in 3 steps. First, those amino or carboxylic groups which are not to participate in the synthesis reaction must be chemically blocked. This also applies to other groups in the molecule which may react during the synthesis of the dipeptide (for example, the hydroxy, the mercapto or the oxo group in the proline analog substituent (V) and in the proline analog (IV), respectively). The qualifications of potential blocking agents that render them suitable for use in the synthesis of the dipeptide of formula A include:

(1) Their introduction should proceed quantitatively and, if optically active amino acids are employed, without racemization of the amino acids involved;

(2) The blocked amino acid must be stable to the conditions employed in the synthesis reactions;

(3) The blocking group must be readily removed under conditions in which the peptide bond is stable and in which, in case of optically pure amino acids, no racemization of the dipeptide occurs.

The most generally useful blocking groups for the synthesis of the dipeptide are the following.

Carboxyl groups are generally blocked through formation of the corresponding lower alkyl or silyl, e.g. tri(lower)alkylsilyl or triaryl(6–12C)silyl, such as optionally substituted triphenylsilyl or benzyl esters. The esterifications are accomplished by conventional means that will be described in more detail below. Once the dipeptide structure corresponding to formula A is produced the lower alkyl groups are hydrolyzed by basic or mild acid conditions as described in more detail below. The benzyl group may be removed by hydrolysis or, preferably, by hydrogenation, in particular by catalytic hydrogenation over palladium as described in more detail below.

A greater range of reagents is employed for the blocking of the amino function. Representative blocking groups include halocarbonates such as (6–12C)aryl lower alkyl halocarbonates such as benzyl halo carbonates or biphenylalkyl halo carbonates, in particular benzylchlorocarbonate; tertiary alkyl halocarbonates such as tertiary-butylhalocarbonates, in particular t-butylchlorocarbonate (BOC)-Cl or di(lower alkyl)dicarbonates, in particular di-(t-butyl)dicarbonate; triphenylmethyl halides such as triphenylmethyl chloride; and trifluoroacetic anhydride.

Reaction of the amino group with (6–12C)aryl halocarbonates, in particular, benzylchlorocarbonate yields the corresponding carboaryloxy derivatives, in particular the benzyloxycarbonyl (or carbobenzoxy symbolized by CBZ) derivative:

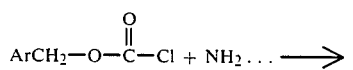

-continued

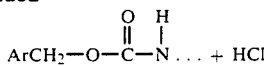

The aralkyloxycarbonyl function, in particular the CBZ function, is readily removed by treatment with acids such as HBr in glacial acetic acid, catalytic reduction such as catalytic hydrogenation over palladium, or with sodium in liquid ammonia.

Triphenylmethyl (trityl) derivatives of the amino group are produced employing triphenylmethyl chloride according to the following equation:

$$(Ph)_3C{-}Cl + H_2N{-}\ldots \rightarrow (Ph)_3C{-}NH{-}\ldots + HCl$$

This group is readily removed by hydrogenation, in particular catalytic hydrogenation over palladium; or hydrolytically with acids in a manner known per se. Related reactions are available for the introduction and removal of other amino-group blocking agents.

In the compounds of formula A the carbon atom to which $R^5$ is attached is asymmetric. In addition, by definition one of the carbon atoms to which $R^2$ and $R^3$ is attached is also asymmetric. For the preferred compounds of formula A, $R^2$ or $R^3$ is a substituent other than hydrogen, i.e. lower alkyl optionally omega-substituted with phenyl or naphthyl. For these compounds, the third carbon to which $R^2$ or $R^3$ is attached is also asymmetric. The compounds accordingly exist in diastereoisomeric forms or in mixtures thereof. The synthesis of the dipeptides can utilize racemates, enantiomers or diastereomers as starting materials. When diastereomeric products result from synthetic procedures, the diastereomeric products can be separated by conventional methods, e.g. chromatographic methods or fractional crystallization.

In general, the amino acid sub-structures having two or more asymmetric carbon atoms in the compounds of formula A are preferred in the (S)-configuration.

All the reactions carried out on the derivatives of the amino acids of which the dipeptide of formula A is composed, and all reaction conditions chosen for the preparation of these dipeptides and the conversion of the dipeptide derivatives into other dipeptide derivatives (for example, esters to amides or esters to the free acids) have to take into account the temperature dependence or relative thermodynamic instability of the amino acids and dipeptide derivatives involved. Therefore, the reaction temperatures employed in steps (a) through (s), in general, will be in the range between −30° C. to 100° C., and preferably shall not exceed 50° C.

The salts of the compounds of formula A may be formed by conventional means. Preferably the free acid or the free base forms of the formula A are reacted with 1 or more (up to 2) equivalents of the appropriate salt-forming base or acid in a solvent or medium in which the salt is insoluble, or in a solvent which can be removed in vacuo or by freeze-drying, or by exchanging the cations of an existing salt for another cation on a suitable ion exchange resin. The conventional salt formation is carried out at temperatures between −20° to 50° C., preferably at about room temperature.

In summary, the invention provides a process for the preparation of a compound of one of the previously described groups (1 to 14) having the general formula (A)

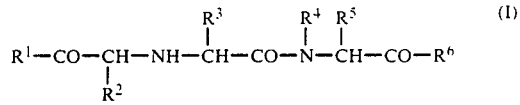

wherein $R^1$, $R^2$, $R^3$, $R^4$, $R^5$ and $R^6$ have the meanings (varied in accordance with Groups 1 to 14), and a salt thereof.

The process comprises:

(a) hydrolyzing a compound of the formula

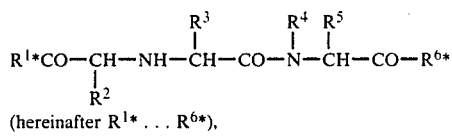

(hereinafter $R^{1*} \ldots R^{6*}$), wherein $R^{1*}$ and $R^{6*}$ are hydroxy, lower alkoxy or benzyloxy and at least one of $R^{1*}$ and $R^{6*}$ is lower alkoxy or benzyloxy to a compound of formula A wherein $R^1$ and $R^6$ are hydroxy;

(b) hydrogenolyzing (reductively cleaving) a compound of the formula $$R^{1*} \ldots R^{6*}$$

wherein $R^{1*}$ and $R^{6*}$ are hydroxy, lower alkoxy or benzyloxy and at least one of $R^{1*}$ and $R^{6*}$ is benzyloxy to a compound of formula A wherein at least one of $R^1$ and $R^6$ is hydroxy;

(c) reducing a compound of the formula

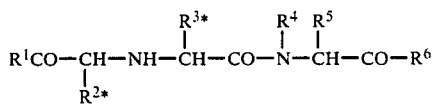

wherein one of $R^{2*}$ or $R^{3*}$ is oxo-substituted lower alkyl optionally ω-substituted with phenyl or naphthyl, and the other of $R^{2*}$ and $R^{3*}$ is (2) of the groups of compounds 1 to 14;

(d) reacting a compound of formula A with a base to form a salt of the compound of formula A;

(e) reacting a compound of formula A with an acid to form an acid addition salt of the compound of formula A;

(f) condensing an amino acid derivative of the formula

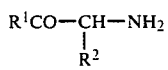

with an α-ketoacid derivative of the formula

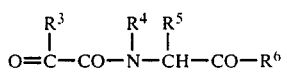

under reductive conditions to form a compound of formula (A);

(g) reducing a Schiff base of the formula

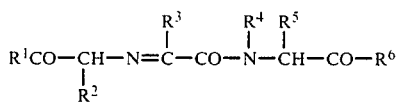

to a compound of formula A;

(h) condensing an α-ketoacid derivative of the formula

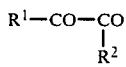

with a dipeptide of the formula

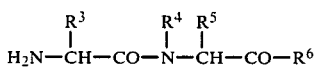

under reductive conditions;

(i) condensing an amino acid derivative of the formula

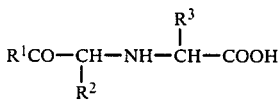

with proline or a proline analog derivative of the formula

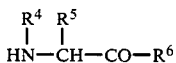

to form a compound of formula A;

(j) alkylating a dipeptide of the formula

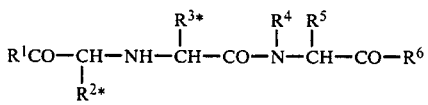

wherein one of $R^{2*}$ and $R^{3*}$ is $-(CH_2)_nNH_2$ and the other of $R^{2*}$ and $R^{3*}$ is (1) of the groups of compounds 1 to 14 with an alkylating agent of the formula

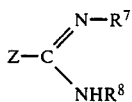

wherein Z is $HSO_3-$, chloro, bromo or iodo, or a lower alkyl mercapto group;

(k) esterifying a compound of the formula

wherein at least one of $R^{1*}$ and $R^{6*}$ is hydroxy and the other is hydroxy, lower alkoxy or benzyloxy with a lower alkanol or benzyl alcohol;

(l) alkylating a compound of the formula

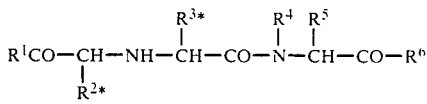

wherein one of $R^{2*}$ and $R^{3*}$ represents an omega-guanidino-substituted alkylene group with 3 to 5, preferably 4, carbon atoms and the other of $R^{2*}$ and $R^{3*}$ is (1) of the groups of compounds 1 to 14 with a lower alkyl alkylating agent optionally substituted with 1 to 5 fluorine atoms;

(m) alkylating a dipeptide derivative of the formula

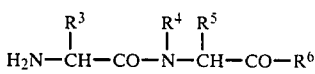

with an alkylating agent of the formula

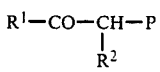

wherein P is halo selected from the group of chloro, bromo or iodo, or is a sulfonyloxy group;

(n) alkylating an amino acid derivative of the formula

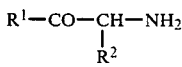

with an alkylating agent of the formula

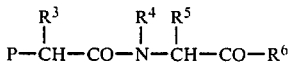

wherein P has the meanings of step (m);

(o) alkylating a guanidino derivative of the formula

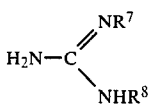

with an alkylating agent of the formula

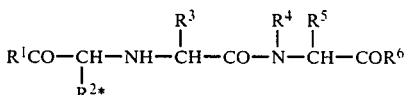

wherein one of $R^{2*}$ and $R^{3*}$ is an alkylating group of the formula

and P has the meanings of step (m), and the other of $R^{2*}$ and $R^{3*}$ is (1) of the groups of compounds 1 to 14;

(p) converting an acid addition salt of the dipeptide of formula A with base to the dipeptide of formula A or a salt thereof with said base;

(q) converting a salt of a dipeptide of formula A (derived from a base) with acid to the free dipeptide of formula A or an acid addition salt thereof;

(r) converting a salt of the dipeptide of formula A, preferably a soluble salt to another salt of the dipeptide of formula A, preferably less soluble than said soluble salt; and (s) acylating ammonia, a lower alkyl amine or a di(-lower)alkyl amine with a dipeptide derivate of the formula $R^{1*} \ldots R^{6*}$ wherein $R^{1*}$ and $R^{6*}$ are hydroxy, chloro, bromo, lower alkoxy, benzyloxy, a lower alkanoyloxy group, or amino optionally substituted with one or two lower alkyl groups, and at least one of $R^{1*}$ and $R^{6*}$ is hydroxy, chloro, bromo, lower alkoxy, benzyloxy, or a lower alkanoyloxy group.

Step (a) of Approaches 7 and 8 involves the hydrolysis of one or both lower alkoxy or benzyl esters of the substructures $R^1$—CO— or —CO—$R^6$. Any conventional hydrolytic conditions may be employed which do not affect the peptide bond —CO—N($R^4$)— or racemize the dipeptide in case diastereomeric products are the desired end products. The hydrolysis of step (a) is carried out under acid or basic conditions and leads to the diacid form, which is thought to be the biologically active form. The reaction temperature for the hydrolysis will be in the range of 0° to 70° C. and the reaction will be carried out in an inert solvent containing water or in water. In general, the acid employed will be between 0.1 and 2 normal. If the reaction is carried out under basic conditions, the solution will be 0.1 to 2 normal with respect to the base employed. If the reaction is carried out under basic conditions, in order to obtain the diacid, the reaction mixture will have to be acidified with acid, such as hydrochloric, acetic or sulfuric acid. The acidification will be carried out between −20° and 40° C., since the peptide bond is sensitive to temperature, particularly if the dipeptide is present in enantiomeric form. Temperatures between −20° and 30° C. are preferred.

Appropriate acids for the acid hydrolysis of Step (a) are inorganic and organic acids. The following inorganic acids can be used: hydrochloric acid, hydrobromic acid, sulfuric acid, nitric acid, phosphoric acid, and the like.

The following organic acids can be used for the acid hydrolysis: trifluoroacetic acid, trichloroacetic, citric or oxalic acid, and the like.

The following inorganic bases can be used for the basic hydrolysis: sodium hydroxide, potassium hydroxide, calcium hydroxide and the like. The following organic bases can be employed for basic hydrolysis: trimethylamine, triethylamine, dicyclohexylamine and the like.

The amides of formula A can be hydrolyzed in a manner known per se to the dipeptides of formula A in water or inert solvents containing water using bases or acids as catalysts. The reaction proceeds between −20° to 100° C.

Step (b) of Approach 7 and 8 involves the hydrogenolysis of benzyl esters. It is self-evident that hydrogenolysis is the method of choice for the production of the two monoesters of Formula A: the compounds wherein $R^1$ is hydroxy and $R^6$ is lower alkoxy and the compounds in which $R^1$ is lower alkoxy and $R^6$ is hydroxy because the hydrogenolysis will not remove the lower alkoxy groups. The monoesters are thought to be prodrugs.

The hydrogenolysis is generally carried out catalytically by hydrogen in the presence of a noble metal, preferably on a carrier, for example, palladium or platinum or rhodium on a carrier such as carbon, or by hydrogen in the presence of Raney nickel. The inert carrier such as carbon will generally contain 5 to 30, preferably 10 percent of the noble metal, in particular palladium. The reaction temperature will be between 0° and 40° C., preferably at about room temperature, under atmospheric pressure or super-atmospheric pressure (up to 10 atm). The reaction times generally range between 30 minutes to 24 hours.

Step (c) of Approaches 5 and 6 involves the reduction of a carbonyl group in one of the side chains $R^2$ and $R^3$. A variety of reduction conditions and reducing agents are applicable. If enantiomeric products are desired, these conditions must not racemize the dipeptide. If $R^1$ or $R^6$ is a benzyloxy group which must be removed, catalytic hydrogenation is the method of choice. Catalytic hydrogenolysis by the above described conditions, for example, contact with molecular hydrogen and 10 percent palladium on carbon will not only reduce the oxo function but also will remove the benzyl ester group to form a compound of Formula A. However, other reductive conditions under mild temperatures such as modified Wolff-Kishner reductions with hydrazine are also applicable.

Step (f) of Approach 2 and step (h) of Approach 3 involve reductive condensations. In both steps an α-ketoacid derivative is condensed with a free amino group (of an amino acid in step (f) or of a dipeptide in step (h)). The reaction is carried out either in an aqueous solution, optimally in a roughly neutral aqueous solution, or in a suitable organic solvent. The following solvents are suitable, for example nitriles such as acetonitrile, propionitrile, cyclic ethers such as THF or dioxane, lower alkanols such as methanol, ethanol, isopropanol, hydrocarbons such as benzene, toluene and the like or mixtures of these solvents. The reaction conditions correspond to those of a Schiff condensation.

In order to reduce the intermediate Schiff base directly which is the condensation product, the reaction can be carried out in the presence of a reducing agent such as a borohydride complex, for example, sodium cyanoborohydride. The reaction proceeds between 0° C. and 40° C., preferably at about room temperature.

In a preferred embodiment of reductive condensation step (f), the amino acid of step (f) in the form of its ester is condensed with the α-ketoacid derivative as follows:

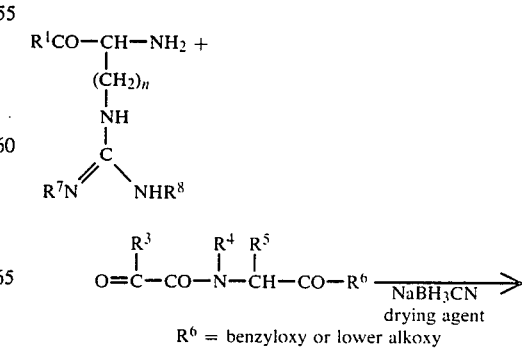

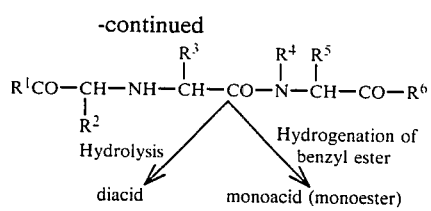

The reaction is carried out in the presence of a drying agent, for example, CaSO$_4$, 4 Å molecular sieves or the like. Hydrogenolysis or hydrogenation, using hydrogen over Pd removes any benzyl group from proline or the proline analog. If R$^1$ is lower alkoxy the monoacid (monoester) is prepared. Mild acid or basic hydrolysis produces the diacid.

Alternatively, if the condensation is carried out without a reducing agent being initially present, the Schiff base of step (g) will be formed which is an enamine which may be catalytically reduced by hydrogen under conditions described above using, for example, as catalyst palladium or platinum on carbon or Raney nickel and the like. Again, 10 percent palladium on carbon, or Raney nickel are the catalysts of choice.

Step (i) of Approach 1 constitutes the classical formation of the peptide bond. This may be accomplished through activation of the carboxyl group in several fashions. The principal pitfall to be avoided is racemization of the amino acids during the reaction. Racemization yields several products that are frequently very difficult to separate. Suitably activated forms of the carboxyl groups include carboxylic acid chlorides (where, however, sometimes racemization occurs), nitro-substituted (6 to 12C)aryl esters, in particular p-nitrophenyl esters, cyanomethyl esters and thioesters. In each case these activated derivatives react smoothly with the amino function or with the imino function of proline, a proline derivative, a proline analog or its derivatives.

In addition, other methods are available that avoid the synthesis of carboxyl-activated intermediates. Preferably the methods involve carbodiimides, such as dicycloalkyl(3-7C)carbodiimides, in particular dicyclohexylcarbodiimide (DCCI), as dehydrating agents. It is assumed that this synthesis would proceed as follows:

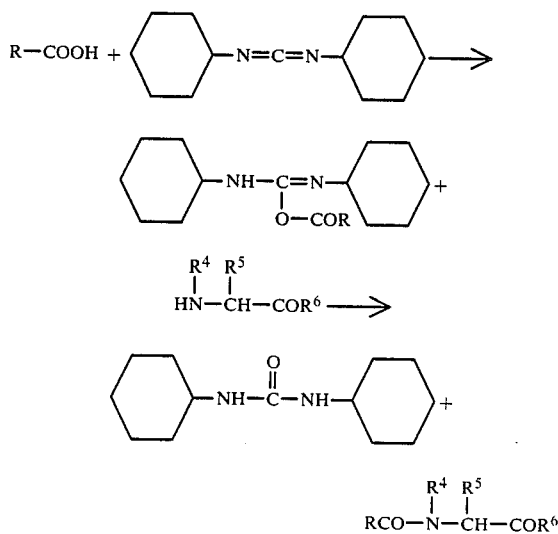

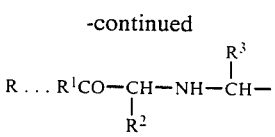

Other condensing or dehydrating agents include diarylphosphoryl azides (with 6 to 12 carbons in the aryl group), in particular diphenylphosphoryl azide (DPPA) or the carbocylic function of the amino acid derivative of step (i) may be activated with esters derived from 1-hydroxybenzotriazole and the like. The condensation step is carried out between 0° and 40° C., preferably at about room temperature.

The dipeptides of formula A can also be produced using the known solid-phase technique, in particular using as solid phase polyamide resins that are swellable by polar solvents such as water. After completion of the synthesis the dipeptide will be removed from the polyamide by hydrolysis, hydrogenolysis, or transesterification.

In general, the condensation reaction conditions will correspond to those used in methods known in the art applied to compounds sensitive to temperature and racemization.

In alkylation step (n) of Approach 2, alkylation step (m) of Approach 3, alkylation step (j) of Approach 4, an amino acid derivative, or a dipeptide with a free amino group, are alkylated with an appropriate alkylating agent. In step (1) of Approach 10 a guanidino-substituted dipeptide is alkylated. In alkylation step (o) of Approach 11 a dialkyl substituted guanidine is alkylated by a dipeptide functioning as an alkylating agent.

In step (n) the alkylating agent is an α-halo-acyl or α-sulfonyloxyacyl amino acid derivative and the reaction will be conducted under basic conditions in water or in another solvent containing the substrate to be alkylated and adding the alkylating agent. The reaction temperature will be kept between −20° and 70° C., preferably at about room temperature. The nature of the acyl group depends on the choice of the substituent R$^3$. For example, α-Chloro- or α-bromoacetylated aminoacids can be used as alkylating agents.

In step (m) a dipeptide is dissolved in an appropriate solvent and is alkylated with the appropriate α-haloacid (ester or amide) or E-sulfonyloxy acid (ester or amide) under basic conditions in water or an organic solvent. The temperature will be kept between 0° and 70° C., preferably at about room temperature. The α-halogen is chloro, bromo, or iodo or P can be a lower alkylsulfonyloxy, halogenated lower alkylsulfonyloxy, e.g. trifluoromethylsulfonyloxy, or a (6 to 12C)arylsulfonyloxy group.

In step (j) the dipeptide is alkylated with an alkylating guanidino derivative substituted by HSO$_3$-, halo, i.e., chloro, bromo, or iodo, or a (lower alkyl)thio group (guanylating agent). The reaction may be conducted by reacting the dipeptide with an S-alkyl isothiourea derivative to form the compounds of Formula A. Preferred is an S-methyl isothiourea. In the alkylation with an S-methyl isothiourea, the methylmercapto group will be the leaving group. More preferably, the reaction is conducted by reacting the dipeptide with a formamidinesulfonic acid, e.g. N,N'-diethylformamidinesulfonic acid. The use of a formamidinesulfonic acid is disclosed in copending and commonly assigned U.S. patent application Ser. No. 06/905,827, filed Sept. 10, 1986 (Arzeno et al.), the disclosure of which is incorporated herein by reference. The reaction is carried out in a suitable aqueous or organic solvent or solvent mixture under basic conditions (pH above 9, preferably at about 10.5) at 0° to 70° C.

Alkylation step (1) is carried out by alkylating the dipeptide of this step with a lower alkyl alkylating agent optionally substituted with 1 to 5 fluoro atoms on other than the α-carbon. The alkylating agent will have as leaving group either chloro, bromo, or iodo or sulfonyloxy. Examples for such alkylating agents are: methyl bromide, methyl iodide, 2,2,2-trifluoro-1-bromoethane, n-hexyl bromide, etc. This reaction is carried out under basic conditions in water or in an organic solvent in the presence of base which accepts the hydrochloric, hydrobromic or hydroiodic acid formed under the alkylating conditions. The temperature will be between 0° to 70° C., preferably at about room temperature.

In alkylation step (o) the dipeptide contains an alkylating group with an ω-halo or ω-sulfonyloxy group for the alkylation of the guanidino derivative. The reaction employs strongly basic conditions, preferably a suitable organic solvent such as DMF, acetonitrile, propionitrile, dioxane and the like.

Esterification step (k) is carried out by classical esterification procedures. In the reaction lower alkanols or benzyl alcohol react with the dipeptide of formula A in the presence of strong inorganic or organic acids under the removal of water. The following inorganic acids can be used: hydrochloric acid, hydrobromic acid, sulfuric acid, and the like. The following organic acids can be used: trifluoroacetic acid, sulfonic acids such as perfluorosulfonic, toluenesulfonic acid, and the like. However, the esters of formula A can also be produced using diazoalkenes in particular diazomethane which will give the methyl ester. The reaction will usually be carried out in an inert solvent. Another method that can be used is the reaction of a metallic salt of a compound of formula A which reacts with a lower alkyl or benzyl halide to form a corresponding lower alkyl or benzyl ester. The sodium or cesium salt of the dipeptide or other metal salts can be used to obtain the ester in good yields. In addition, salts of tertiary amines such as 1,8-diazabicyclo[5.4.0]undec-7-ene, or tri(lower)alkyl amines, in particular triethylamine can employed because of their better solubility.

In another modification of step (k) the esterification is carried out by reacting an acyl halide or diacyl halide of a compound of formula A with a lower alkanol or with benzyl alcohol. This leads to a rapid formation of the ester. In the reaction, 1 mole of the acyl halide is reacted with at least 2 moles of the lower alkanol or benzyl alcohol and the reaction proceeds smoothly to obtain the corresponding diester. In a preferred embodiment the reaction is facilitated by the formation of an adduct with thionylchloride and the lower alkanol or benzyl alcohol at temperatures below 0° C. which reacts quickly to form the ester.

In another modification of the process a mixed acid anhydride of the dipeptide of formula A is reacted with an alkanol or benzyl alcohol. The reaction is catalyzed by tertiary organic bases such as pyridine.

It is understood that in condensation step (f) and (h) under reductive conditions the α-ketoacid derivative can be the free acid or its ester. The amino acid derivative or the dipeptide derivative can be in the form of the free acid or of the ester, amide or hydroxamic acid.

In the alkylation steps, the alkylating agent of steps (n) and (o) may be in the form of the free acid, its ester, or its amide. The amino acid or dipeptide derivative in all these alkylating steps may also be present in the form of their esters or amides.

The amides of the peptides of formula A in which at least one of $R^1$ and $R^6$ is the amino group optionally substituted with one or two lower alkyl groups are prepared by common methods known for the preparation of amides. If only one of $R^1$ and $R^6$ is an optionally substituted amino group the compounds are monoamides, whereas if both $R^1$ and $R^6$ are an optionally substituted amino group these dipeptides are diamides.

Ammonia or lower alkyl or dialkyl amines can be reacted directly with derivatives of the formula A, in particular lower alkyl esters or acid chlorides or acid anhydrides which function as acylating derivatives. Ammonia and the lower alkyl amines (primary amines) and the di(lower alkyl)amines (secondary amines) react very smoothly with these acylating agents. With anhydrides the reaction can be even conducted in aqueous solution. The reaction with acyl halides requires two moles of amine or ammonia, only one of which will be acylated because the second mole combines with the hydrogen halide formed in the reaction. If the acylating agent is an anhydride only one mole of amine or ammonia can be used because the free acid formed is a weak acid and the salt of a weak base and the weak acid dissociates to produce the acylated amine when heated with an excess of the anhydride. Therefore all the amine can be converted into amide by this procedure. If esters are used as acylating agents again the amine and the ester acylation will be reacted in an approximate molar ratio of one to one. The acylation can be conducted in non-acqueous solutions, i.e., in inert solvents such as DMF, lower alkanols such as methanol (or ethanol), and the like. The reaction temperatures will be between $-20°$ and $+40°$ C. preferably at about 35° C.

The conversions of steps (p), (q) and (r) are usually carried out in inert solvents at temperatures between $-20°$ and 50° C., preferably between $-10°$ and 30° C. In step (p) the acid addition salt of the dipeptide (which may be mono- or dibasic) is treated with the appropriate equivalent amount of base to form the monobasic salt, the free dipeptide or to form its salt with the base. In step (q) the dipeptide salt with base is the starting material and treated with the appropriate equivalent of acid to form the monobasic salt, the free dipeptide or the acid addition salt (which contains one or two protonated nitrogens).

It is understood that the free dipeptides of formula A exist in a zwitterionic form, any carboxylic groups being dissociated ($-COO^-$) and the imino group (s) or the $=N-R^7$ group being associated with a proton.

In step (r) a salt of a dipeptide is reacted with an inorganic or organic salt to precipitate a less soluble salt (double decomposition). Alternatively, this exchange can be carried out with appropriately charged ion exchange resins.

The starting materials of steps (c), (f), (g), (h), (i), (j), (l), (m), (n) and (o) are either known from the literature or can be made by known methods from known starting materials (e.g. European Patent Application Nos. 12401, 65301 and 79022, the disclosures of which are incorporated herein by reference). For example, the oxo substituted compound of step (c) can be produced by the following reaction scheme:

REACTION SCHEME I

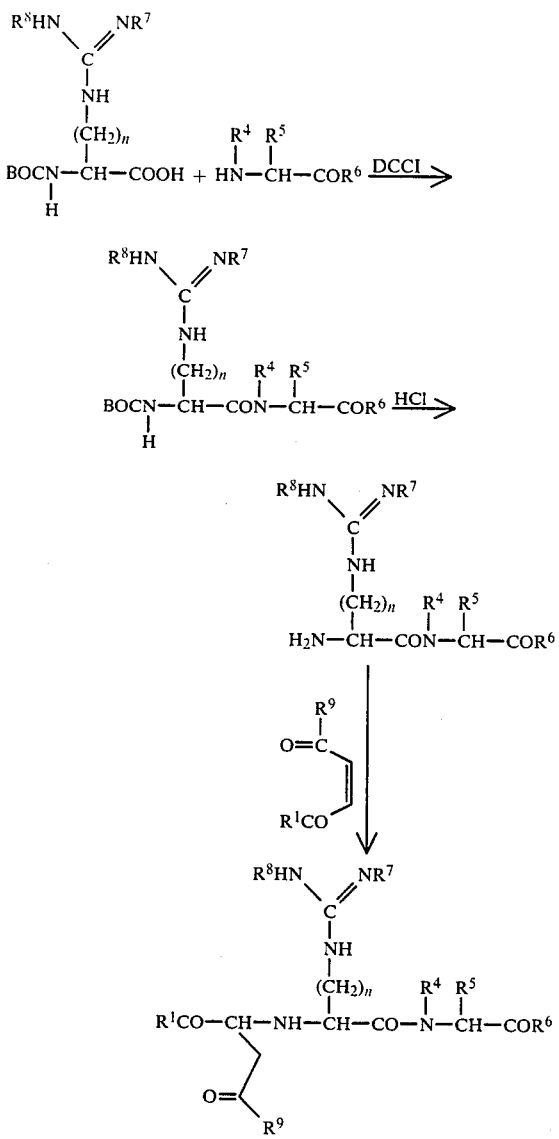

R⁹ is alkyl(1-4C), phenyl, naphthyl.

In Reaction Scheme I, the BOC-protected guanidino-substituted amino acid is first coupled to a proline ester, or a proline analog ester (e.g., benzylprolinate or a benzylprolinate analog) using, for example, DCCI as dehydrating agent thus forming a dipeptide. The dipeptide is then deprotected with HCl/ethyl acetate to obtain the free amino group which is reacted in a Michael-like reaction with an unsaturated Michael acceptor such as a lower alkyl (benzoyl, naphthoyl or lower alkanoyl)-substituted acrylate or a corresponding benzyl acrylate. Ethyl 3-benzoylacrylate is a preferred Michael acceptor. The Michael-like addition results in the protected starting material for step (c).

The starting material of step (c) can also be obtained by Mannich condensation of a ketone of the formula $R^{2*}$—COCH₃ (wherein $R^{2*}$ is phenyl, naphthyl or lower alkyl with one to four carbon atoms) with a glyoxylic acid derivative (in particular a glyoxylic acid ester) and the dipeptide derivative of step (m). The Mannich condensation will be conducted at temperatures between 20° and 50° C., preferably 40° to 50° C. in the presence of a dehydrating agent such as glacial acetic acid.

The starting materials of steps (f), (g), and (h) can be produced using the methods described in European Patent Applications Nos. 12401 and 65301 or are known compounds or can be made from known compounds. Alternatively, the amino acid derivative of step (f) can be produced by the method of Arzeno et al., U.S. patent application Ser. No. (Case No. 25710), referred to previously, as follows:

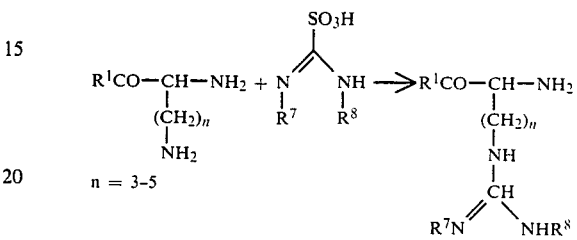

n = 3-5

An α,ω-diaminocarboxylic acid is alkylated with a formamidinesulfonic acid derivative to form an α-amino-ω-(di(lower alkyl)guanidino)carboxylic acid. When n equals 4 the α,ω-diaminocarboxylic acid is lysine. If lysine is used the resulting guanylated acid is a homolog if the naturally occurring amino acid arginine. In a preferred embodiment $R^1$ will be hydroxy. The α-amino-ω-(di(lower alkyl)guanidino)carboxylic acid can be converted to the corresponding lower alkyl or benzyl esters, for example by reaction at low temperature with the lower alkanol (or benzyl alcohol) and thionyl chloride or the lower alkanol (or benzyl alcohol) and oxalyl chloride (e.g., P. A. Sadler, *Helv. Chim. Acta*, 61, 1675 (1978) and references therein).

The proline analogs of step (i) are either known compounds or known natural amino acids or imino acids easily produced by methods known in the art (European Patent Application Nos. 65301 and 79022). The alkylated amino acid derivative of step (i) is obtained by alkylation of the amino acid H₂N—CH(R³)—COOH with a suitable alkylating agent R¹CO—CH(R²)—P wherein P has the above described meanings. This reaction is carried out under normal alkylating conditions between 0° and 40° C., as described above. Alternatively, the alkylated amino acid derivative of step (i) can be obtained by appropriate alkylation of the amino acid R'CO—CH(R²)—NH₂ with

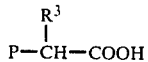

by methods described above.

The dipeptide of step (j) is obtained according to methods described in European Patent Application Nos. 12401, 65301 and 79022. The alkylating agents of step (j) are well-known compounds. Likewise, the preparation of the dipeptide of step (l) is described in European Patent Application Nos. 12401 and 79022.

The dipeptide derivative of step (m) is obtained by classical peptide condensation reactions as for example described in European Patent Application Nos. 12401 and 65301. The alkylating agents of step (m) are compounds known in art.

The starting materials of step (n) can be produced by methods following the teaching of European Patent Application No. 12401.

The guanidine derivatives of step (o) are well-known compounds. The alkylating agent of the step (o) can be produced from the dipeptides described in European Patent Application No. 12401, 65301 and 79022 by SN2 reactions. Replacing an ω-hydroxy group by halo selected from the group of chloro, bromo and iodo or a sulfonyloxy group in the side chain ($R^2$ or $R^3$) will lead to the alkylating agents of step (o).

The most important dipeptides of this invention are derived from (S)-1,2,3,4-tetrahydroisoquinoline-3-carboxylic acid (THIQ). With reference to formula A, in this group n is 3 or preferably 4, $R^2$ is the di(lower alkyl)guanidino-substituted radical (2), $R^3$ is a lower alkyl group and $R^1$ and $R^6$ are hydroxy. Particularly preferred dipeptides in this group are characterized as follows:

n=4; $R^2$ is a $N^G,N^{G'}$-diethylguanidinobutyl group (optionally substituted in both ethyl groups with up to 3 fluorine atoms on the β-carbons); $R^3$ is methyl or ethyl.

Compounds in which $R^2$ is a guanidinoalkyl group and $R^3$ is alkyl may be named in several ways. Conventionally, they are named as dipeptides of guanidinoalkyl-substituted amino acids with the proline or proline analogs, but they may also be named as guanidino-containing amino acid derivatives of N-alkanoylproline or proline analogs. Thus, for example, (S)-2-[(S)-N-[(S)-1-carboxy-5-N',N''-diethylguanidinopentyl]-alanyl]-1,2,3,4-tetrahydroisoquinoline-3-carboxylic acid may also be named as (S)-N-[(S)-2-($N^G,N^{G'}$-diethyl-(S)-homoargin-Nα-yl]propionyl]-1,2,3,4-tetrahydroisoquinoline-3-carboxylic acid.

The most preferred compounds are (1) (S)-N-[(S)-2-[$N^G,N^{G'}$-diethyl-(S)-homoargin-Nα-yl]propionyl]-THIQ and its salts;

(2) (S)-N-[(S)-2-[$N^G,N^{G'}$-bis(2,2,2-trifluoroethyl)-(S)-homoargin-Nα-yl]propionyl]-THIQ and its salts;

(3) (S)-N-[(S)-2-[$N^G$-methyl-$N^{G'}$-n-butyl-(S)-homoargin-Nα-yl]propionyl]-THIQ and its salts; and (4) (S)-N-[(S)-2-[$N^G,N^{G'}$-diethyl-(S)-homoargin-Nα-yl]butanoyl]-THIQ and its salts;

The following compounds are also of particular interest:

(5) (S)-N-[(S)-2-[$N^G,N^{G'}$-diethyl-(S)-argin-Nα-yl]propionyl]-THIQ and its salts;

(6) (S)-N-[(S)-2-[$N^G,N^{G'}$-diethyl-(S)-homoargin-Nα-yl]propionyl]-7-methyl-THIQ and its salts;

(7) (S)-N-[(S)-2-[$N^G,N^{G'}$-diethyl-(S)-homoargin-Nα-yl]propionyl]-7-chloro-THIQ and its salts;

(8) (S)-N-[(S)-2-[$N^G,N^{G'}$-bis(2,2,2-trifluoroethyl)-(S)-homoargin-Nα-yl]propanoyl]proline and its salts;

(9) (S)-N-[(S)-2-[$N^G,N^{G'}$-diethyl-(S)-homoargin-Nα-yl]-4-phenylbutanoyl]proline and its salts; and

(10) (S)-N-[(S)-2-[$N^G,N^{G'}$-diethyl-(S)-homoargin-Nα-yl]propanoyl]-2-carboxy-2,3-dihydroindole and its salts.

The compounds (1) to (10) and the other compounds prepared according to the examples below can be prepared employing the methods of steps (i), (f), (n), (h), (m), (j), (c), (a), (b), (g), (l), (o), (p), and (q) described below. The preferred methods for the preparation of the preferred compounds are the methods incorporated in steps (i), (f), (n), (h), (m), (c), (a), and (b). Even more preferred are the methods of steps (i), (f), (h), (c), and (a), in particular with regard to compound (1).

In the most preferred compounds of formula A, there is a carbon chain uninterrupted by hetero atoms between the $N^G,N^{G'}$-dialkylguanidino substituent (a substituent of undiminished basicity) and the carboxy group $R^1$CO— (in which $R^1$ is hydroxy) with a chain length of no less than four and no more than six carbon atoms. A chain length of five carbon atoms yields the compounds with the greatest ACE inhibition.

EXAMPLES

The following Preparation and Examples illustrate this invention but should not be considered to limit its scope.

Preparation 1

13.17 g of benzyl (S)-1,2,3,4-tetrahydroisoquinoline-3-carboxylate tosylate (N. Yoneda, et al., *Chem.Pharm. .Bull.*, 31, 312 (1983)) was suspended in 30 mL CHCl$_3$. N-methylmorpholine was added until the pH was 7, 6.8 g of dicyclohexylcarbodiimide and 3.17 g of pyruvic acid was added at −5° C. The reaction mixture was stirred at −50° C. for one hour and 0° C. for 48 hours. The reaction mixture was filtered, and the filtrate was concentrated to dryness to give a semi-solid, which was purified by passing through a silica gel column and eluting with ethyl acetate:hexane (1:1) to give benzyl N-pyruvoyl-(S)-1,2,3,4-tetrahydroisoquinoline-3-carboxylate as a yellow oil, $[\alpha]_D^{25}$ −10.3°.

Example 1

This Example shows the synthesis of (S)-N-[2-[$N^G,N^{G'}$-diethyl-(S)-homoargin-Nα-yl]-propionyl]-1,2,3,4-tetrahydroisoquinoline-3-carboxylic acid, and exemplifies Approach 2, Step (f), Approach 8, Step (a), and Approach 7, Step (d).

1.8 g (5.34 millimoles (mmol)) benzyl N-pyruvoyl-(S)-1,2,3,4-tetrahydroisoquinoline-3-carboxylate (1), 1.65 g (5.34 mmol) ethyl $N^G,N^{G'}$-diethyl-(S)-homoarginate hydrochloride (for description of synthesis, see J. J. Nestor, Jr. et al., "Peptides—Structure and Function", *Proc. Eighth Amer. Peptide Symposium*, V. J. Hruby and D. H. Rich, Eds., Pierce Chem. Co., Rockford IL, 1984, pp. 861-4), 0.58 g (5.87 mmol) potassium acetate, and 1 g calcium sulphate were mixed together in 10 mL of anhydrous ethyl alcohol and stirred at room temperature for 48 hours. Then, 0.37 g (5.87 mmol) sodium cyanoborohydride in 5 mL ethyl alcohol was added at room temperature over a period of 3 hours. The reaction mixture was further stirred at room temperature for 3 more hours, and was then acidified to a pH of about 4 with 1N hydrochloric acid. The reaction mixture was filtered through Celite and then concentrated to dryness.

The residue was partitioned between an organic phase of ethyl acetate and an aqueous phase of 1N hydrochloric acid. The hydrochloric acid solution was passed through an Amberlite XAD-2 resin column and first eluted with water and then a gradient of water to ethanol. Concentration of the appropriate fractions gave about 1.5 g of a yellowish oil. The oil was further purified by preparative reverse phase HPLC on a 2.5×100 cm column of Lichroprep RP-18 (20–40μ diameter, E. Merck) using an 80% CH$_3$CN: 20% H$_2$O (0.03M in NH$_4$OAc, pH 7) eluent (17 mL/min) to give 1.4 g of yellow oil. The oil was hydrolyzed in a solution of 0.25 g sodium hydroxide in 10 mL water. The reaction mixture was stirred at room temperature for 1 hour, then acidified to about pH 4 with hydrochloric acid. The reaction mixture was passed through XAD again, eluted with water and then a gradient of water to ethanol. The crude product obtained was further purified by preparative HPLC on the column described above, but with an 18% $CH_3CN$: 72% $H_2O$ (0.03M in $NH_4OAc$, pH7) eluent to give 350 mg of the desired product, m.p. 140°–150° C.

Similarly by the use of this procedure,
(S)-N-[2-[$N^G$,$N^{G'}$-diethyl-(S)-homoargin-N$\alpha$-yl]propionyl]proline acetate;
(S)-N-[2-[$N^G$,$N^{G'}$-diethyl(S)-homoargin-N$\alpha$-yl]propionyl]-1,2,3,4-tetrahydroisoquinoline-3-carboxylic acid acetate;
(S)-N-[2-[$N^G$,$N^{G'}$-diethyl-(S)-homoargin-N$\alpha$-yl]propionyl]-2,3-dihydroindole-2-carboxylic acid acetate;
(S)-N-[2-[$N^G$,$N^{G'}$-diethyl-(S)-homoargin-N$\alpha$-yl]propionyl]-1-azabicyclo[3.3.0]octane-2-carboxylic acid acetate;
(S)-N-[2-[$N^G$,$N^{G'}$-bis(2,2,2-trifluoroethyl)-(S)-homoargin-N$\alpha$-yl]propionyl]-1,2,3,4-tetrahydroisoquinoline-3-carboxylic acid acetate; m/s [MH+$H_2O$] 565; and
(S)-N-[2-[2-[$N^G$-methyl-$N^{G'}$-(n-butyl)-(S)-homoargin-N$\alpha$-yl]propionyl]-1,2,3,4-tetrahydroisoquinoline-3-carboxylic acid acetate were prepared.

If the final saponification with NaOH is not performed, the corresponding ethyl esters are obtained.

Preparation 2

This preparation shows the synthesis of benzyl [N$\alpha$-t-butoxycarbonyl-$N^G$,$N^{G'}$-diethyl-(S)-homoarginyl]-(S)-prolinate.

760 mg (2 mmol) N$\alpha$-t-butoxycarbonyl-$N^G$,$N^{G'}$-diethyl-(S)-homoarginine hydrochloride was dissolved in 5 mL DMF. 450 mg (2.2 mmol) dicyclohexylcarbodiimide and 299 mg (2.2 mmol) 1-hydroxybenzotriazole (HOBT) was added to the DMF solution. 531 mg (2.2 mmol) benzyl (S)-prolinate hydrochloride was added to the solution. The pH was adjusted to between 8 and 9 with N-methylmorpholine. The reaction mixture was stirred at room temperature overnight and filtered. The filtrate was concentrated to dryness. The residue was partitioned between ethyl acetate and water; and the water layer was concentrated to dryness and passed through silica gel column using a gradient from dichloromethane/methanol (9:1) to dichloromethane/methanol (4:1) as the eluent. The concentrated fractions gave the product as a white foam, $[\alpha]_D^{25}$ −52.9°. Similarly, using this synthetic method:
benzyl N-t-butoxycarbonyl-$N^G$,$N^{G'}$-bis-(2,2,2-trifluoroethyl)-L-homoarginyl-L-prolinate;
benzyl N-t-butoxycarbonyl-$N^G$,$N^{G'}$-dimethyl-L-homoarginyl-L-prolinate;
benzyl N-t-butoxycarbonyl-$N^G$-methyl-$N^{G'}$-n-butyl-L-homoarginyl-L-prolinate; and
benzyl N-t-butoxycarbonyl-$N^G$,$N^{G'}$-di-n-propyl-L-homoarginyl-L-prolinate are made.

Preparation 3

This preparation shows the synthesis of benzyl N-[N$\alpha$-(1-ethoxycarbonyl-3-oxo-3-phenylpropyl)($N^G$,$N^{G'}$-diethyl-L-homoarginyl)]-L-prolinate.

1.3 g (2.2 mmol) benzyl N-t-butyloxycarbonyl-$N^G$,$N^{G'}$-diethyl-L-homoarginyl-L-prolinate was deprotected using 3 mL of saturated hydrochloric acid in ethyl acetate. The deprotected peptide was triturated with diethyl ether, the ether was decanted, and the residue was dried to give 1.1 g of an oil. The oil was dissolved in 5 mL absolute ethyl alcohol, and the pH was adjusted to between 8 and 9 with triethylamine. 0.53 g (2.59 mmol) of ethyl 3-benzoylacrylate was added. The reaction mixture was allowed to stir at room temperature for 2 hours, then stripped to dryness. The residue was partitioned between water and ethyl acetate. The water layer was concentrated to dryness and passed through a silica gel column and eluted with dichloromethane/methanol (4:1). The appropriate fractions were concentrated to give the product as a white foam. Similarly, by the use of this synthetic method,
benzyl N-[N$\alpha$-(1-ethoxycarbonyl-3-oxo-3-phenylpropyl)-($N^G$,$N^{G'}$-bis(2,2,2-trifluoroethyl)-(S)-homoarginyl)]-(S)-prolinate;
benzyl N-[N$\alpha$-(1-ethoxycarbonyl-3-oxo-3-phenylpropyl)-$N^G$-methyl-$N^{G'}$-n-butyl-(S)-homoarginyl)]-(S)-prolinate;
benzyl N-[N$\alpha$-(1-ethoxycarbonyl-3-oxo-3-phenylpropyl)-$N^G$,$N^{G'}$-dimethyl-(S)-homoarginyl)]-(S)-prolinate; and
benzyl N-[N$\alpha$-(1-ethoxycarbonyl-3-oxo-3-phenylpropyl)-$N^G$,$N^{G'}$-di-n-propyl-(S)-homoarginyl]-(S)-prolinate are made, the starting materials for Example 2.

Example 2

This Example shows the synthesis of N-[N$\alpha$-(1-ethoxycarbonyl-3-phenylpropyl)-L-($N^G$,$N^{G'}$-diethylhomoarginyl]-L-proline, exemplifying Approach 6, Step (c), Approach 7, Step (a), Approach 8, Steps (a) and (b) and Approach 14, Step (q).

400 mg of the white foam of Preparation 3 was dissolved in 15 mL acetic acid containing 1.6% concentrated sulfuric acid. 100 mg 10% palladium on carbon was added. The reaction mixture was hydrogenated at room temperature under atmospheric pressure for one and one-half hours before being filtered through Celite and neutralized to pH 3 to 4 with dilute ammonium hydroxide at 0° C. The filtrate was passed through an Amberlite XAD column by elution with a water to ethyl alcohol gradient. The concentration of the appropriate fractions gave about 200 mg of an oil. The oil was further purified by reverse phase preparative HPLC, as described in Example 1, to give 80 mg of one isomer and 40 mg of the other isomer. The compounds are isomeric in position 1 of the phenylpropyl residue and may be used in either the racemic or resolved forms. Similarly, by the use of this synthetic method,
N-[N$\alpha$-(1-ethoxycarbonyl-3-phenylpropyl)-L-($N^G$,$N^{G'}$-bis-(2,2,2-trifluoroethyl)-homoarginyl)]-L-proline;
N-[N$\alpha$-(1-ethoxycarbonyl-3-phenylpropyl)-L-($N^G$-methyl-$N^{G'}$-n-butyl)homoarginyl)]-L-proline;
N-[N$\alpha$-(1-ethoxycarbonyl-3-phenylpropyl)-L-($N^G$,$N^{G'}$-dimethyl)homoarginyl)]-L-proline; and
N-[N$\alpha$-(1-ethoxycarbonyl-3-phenylpropyl)-L-($N^G$,$N^{G'}$-di-n-propyl)homoarginyl]-L-prolinate are made.

Similarly, by incorporation of a conventional saponification step, the corresponding diacids can be obtained.

Preparation 4

This preparation shows the synthesis of benzyl prolinate hydrochloride.

30.2 mL thionyl chloride was added dropwise to 300 mL benzyl alcohol at a temperature between −10° and −5° C. The reaction mixture was stirred at −5° for 15 min. 23.0 g proline was added to the reaction mixture. The reaction mixture was stirred a further one hour at −5° to −10°, then at room temperature. At this time the reaction mixture was homogeneous. The reaction mixture was then added to 1.5 L ethyl ether, and a solid formed. The solid benzyl prolinate hydrochloride was filtered, washed with ether and dried.

Similarly, by the use of this synthetic method, ethyl 2,3-dihydro-indole-2-(S)-carboxylate hydrochloride (mp 163°–165°) was made.

Preparation 5

This preparation shows the synthesis of benzyl N-(2-oxopentanoyl)prolinate.

8.8 g benzyl prolinate hydrochloride, 9.78 g dicyclohexylcarbodiimide and 6.12 g diisopropylethylamine were reacted together in 50 mL dichloromethane at 0°. 5.51 g 2-oxopentanoic acid in 10 mL dichloromethane was added dropwise at 0°. The pH of the reaction was adjusted to between 8 and 9 with diisopropylethylamine. The reaction mixture was stirred for four hours at 0°, then room temperature overnight. The next day, the reaction mixture was filtered, concentrated to dryness, and partitioned between ethyl acetate and water. The organic layer was washed with 5% sodium bisulfate, 5% sodium bicarbonate, and saturated sodium chloride solutions, and dried with magnesium sulfate. The organic layer was concentrated to give a yellow oil. The oil was then passed through a silica gel column and eluted with ethyl acetate/hexane (4:6) and ethyl acetate/hexane (1:1). Benzyl N-(2-oxopentanoyl)prolinate, $[\alpha]_D^{25} - 56.9$, was isolated.

Similarly, by the use of this synthetic method, benzyl N-(2-oxobutanoyl)prolinate, $[\alpha]_D^{25} - 63.8$;

benzyl N-(2-oxopropanoyl)prolinate, $[\alpha]_D^{25} - 62.0$;

benzyl N-(2-oxobutanoyl)-1,2,3,4-tetrahydroisoquinoline-3-(S)-carboxylate hydrochloride, $[\alpha]_D^{25} - 9.87$;

benzyl N-(2-oxoethanoyl)-1,2,3,4-tetrahydroisoquinoline-3-(S)-carboxylate hydrochloride, $[\alpha]_D^{25} - 14.4$; and benzyl-N-(2-oxopropanoyl)-2,3-dihydroindole-2-(S)-carboxylate hydrochloride, $[\alpha]_D^{25} - 101.7$, were made.

EXAMPLE 3

This example shows the synthesis of benzyl N-[2-(O-ethyl-$N^G,N^{G'}$-diethyl-L-homoargin-$N^\alpha$yl)-pentanoyl]-prolinate, exemplifying Approach 2, Step (f).

2.5 g benzyl N-(2-oxopentanoyl)prolinate, 2.3 g ethyl $N^G,N_{G'}$-diethyl-L-homoarginate hydrochloride, and 3 g calcium sulfate were mixed together in 25 mL of absolute ethanol. The resulting mixture was stirred for 48 hrs at room temperature, and 0.5 g sodium cyanoborohydride in 10 mL absolute ethanol was added at 0°. The reaction mixture was stirred at room temperature for 2 hours, acidified with acetic acid to pH of about 4, and filtered. The solvent was removed and the residue partitioned between ethyl acetate and water. The organic layer was washed with saturated sodium chloride solution and dried with magnesium sulfate, filtered, and concentrated to give an oil. The oil was then passed through a silica gel column and eluted with dichloromethane/methanol (8:1) and dichloromethane/methanol (6:1).

Similarly, by the use of this synthetic method, benzyl N-[2-(O-ethyl $N^G,N^{G'}$-diethyl-L-homoargin-$N^\alpha$-yl)butanoyl]prolinate, benzyl N-[2-[O-ethyl $N^G,N^{G'}$-bis(2,2,2-trifluoroethyl)-L-homoargin-$N^\alpha$-yl]propanoyl]prolinate, benzyl N-[2-(O-ethyl $N^G,N^{G'}$-diethyl-L-homoargin-$N^\alpha$-yl)butanoyl]-1,2,3,4-tetrahydroisoquinoline-3-(S)-carboxylate, benzyl N-[2-(O-ethyl $N^G,N^{G'}$-diethyl-L-homoargin-$N^\alpha$-yl)ethanoyl]-1,2,3,4-tetrahydroisoquinoline-3-(S)-carboxylate, and benzyl N-[2-(O-ethyl $N^G,N^{G'}$-diethyl-L-homoargin-$N^\alpha$-yl)propanoyl]-2,3-dihydroindole-2-(S)-carboxylate were made. Many of these intermediates were used without further purification and characterization.

EXAMPLE 4

This example shows the synthesis of N-[2-($N^G,N^{G'}$-diethyl-L-homoargin-$N^\alpha$-yl)-pentanoyl]proline, exemplifying steps (a) and (d) of Approaches 7, 8 and step (h) of Approach 14.

0.8 g benzyl N-[2-(O-ethyl $N^G,N^{G'}$-diethyl-L-homoargin-$N^\alpha$-yl)pentanoyl]prolinate was hydrolysed with a solution of 0.2 g sodium hydroxide in 10 mL water and 2 mL ethanol at room temperature for two hours. After two hours the reaction mixture was acidified to pH of about 4 with acetic acid and filtered. The solvent was removed and the product purified by preparative HPLC. N-[2-($N^G,N^{G'}$-diethyl-L-homoargin-$N^\alpha$-yl)-pentanoyl]proline, m/s $[M+H]^+442$, was isolated.

Similarly, by the use of this synthetic method,

N-[2-($N^G,N^{G'}$-diethyl-L-homoargin-$N^\alpha$-yl)-butanoyl]-proline, $[M+H]^+448$, N-[2-($N^G,N^{G'}$-bis(2,2,2-trifluoroethyl)-L-homoargin-$N^\alpha$-yl)propanoyl]proline, $[M+H]^+522$, N-[2-($N^G,N^{G'}$-diethyl-L-homoargin-$N^\alpha$-yl)-butanoyl]-1,2,3,4-tetrahydroisoquinoline-3-(S)-carboxylic acid, $[M+H]^+490$, N-[2-($N^G,N^{G'}$-diethyl-L-homoargin-$N^\alpha$-yl)ethanoyl]-1,2,3,4-tetrahydroisoquinoline-3-(S)-carboxylic acid (the identity of which was confirmed by NMR data), and N-[2-($N^G,N^{G'}$-diethyl-L-homoargin-$N^\alpha$-yl)propanoyl]-2-(S)-carboxy-2,3-dihydroindole, $[M+H]^+444$, were made.

EXAMPLE 5

The following compounds were prepared using the methods identified in the tabulation below with their corresponding physical constants ($R^1$ = hydroxy, $R^2$ = —(CH$_2$)$_4$NH—C(=NR$^7$)NHR$^8$)

| $R^3$ | $R^4$ $R^5$<br>—N—CH—COOH | $R^7$ | $R^8$ | Method | Physical Constant |
|---|---|---|---|---|---|
| CH$_3$ | THIQ | C$_2$H$_5$ | C$_2$H$_5$ | (i) | m.p. 140–150° C. |
| | | | | (n) | nmr:m/s:[M + H] 476 |
| | | | | (h) | m.p. 142–152° C. |
| | | | | (m) | nmr confirmed |
| | | | | (b) | nmr confirmed |
| CH$_3$ | THIQ | CH$_3$ | n-C$_4$H$_9$ | (i) | |
| | | | | (n) | |

-continued

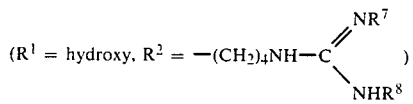
($R^1$ = hydroxy, $R^2$ = $-(CH_2)_4NH-C\begin{matrix}NR^7\\NHR^8\end{matrix}$)

| $R^3$ | $R^4\ R^5$<br>$-N-CH-COOH$ | $R^7$ | $R^8$ | Method | Physical Constant |
|---|---|---|---|---|---|
| | | | | (h) | |
| | | | | (m) | |
| | | | | (b) | |
| | | | | (a) | |
| $CH_3$ | THIQ | $CF_3CH_2$ | $CF_3CH_2$ | (i) | m/s[MH+H$_2$O] 565 |
| | | | | (a) | nmr confirmed |
| $C_2H_5$ | THIQ | $C_2H_5$ | $C_2H_5$ | (j) | [M + H]$^+$ 490 |
| | | | | (a) | [M + H]$^+$ 490 |
| $CH_3$ | 7-$CH_3$—THIQ | $C_2H_5$ | $C_2H_5$ | (i) | |
| | | | | (c) | |
| | | | | (a) | |
| $CH_3$ | 7-Cl—THIQ | $C_2H_5$ | $C_2H_5$ | (e) | |
| | | | | (a) | |
| $CH_3$ | prolin-N—yl | $C_2H_5$ | $C_2H_5$ | (i) | |
| $C_2H_5$ | prolin-N—yl | $C_2H_5$ | $C_2H_5$ | (i) | [M + H]$^+$ 448 |
| | | | | (n) | nmr confirmed |
| $CH_3$ | prolin-N—yl | $CF_3CH_2$ | $CF_3CH_2$ | (j) | [M + H]$^+$ 522 |
| | | | | (n) | nmr confirmed |
| $CH_3$ | 2-carboxy-<br>1,3-dihydro-<br>indol-N—yl | $C_2H_5$ | $C_2H_5$ | (i) | [M + H]$^+$ 444 |
| | | | | (o) | nmr confirmed |
| | | | | (h) | |
| $CH_3$ | THIQ | $CH_3$ | $CH_3$ | (i) | |
| | | | | (n) | |
| | | | | (h) | |
| | | | | (m) | |
| | | | | (b) | |

EXAMPLE 6

A typical tablet of this invention contains (S)-N-[(S)-2-[N$^G$,N$^{G'}$-diethyl-(S)-homoargin-Nα-yl)propionyl]-1,2,3,4-tetrahydroisoquinoline-3-carboxylic acid (25 mg), pre-gelatinized starch USP (50 mg), microcrystalline cellulose (100 mg), and magnesium stearate (1 mg). In a like manner, for example, the ethyl ester of (S)-N-[(S)-2-[N$^G$,N$^{G'}$-diethyl-(S)-homoargin-Nα-yl)propionyl]-1,2,3,4-tetrahydroisoquinoline-3-carboxylic acid may be formulated in place of (S)-N-[(S)-2-[N$^G$,N$^{G'}$-diethyl-(S)-homoargin-Nα-yl)propionyl]-1,2,3,4-tetrahydroisoquinoline-3-carboxylic acid with the composition of pre-gelatinized starch, microcrystalline cellulose, and magnesium stearate described above.

A combination tablet with a diuretic such as hydrochlorothiazide typically contains (S)-N-[(S)-2-[N$^G$,N$^{G'}$-diethyl-(S)-homoargin-Nα-yl)propionyl]-1,2,3,4-tetrahydroisoquinoline-3-carboxylic acid (7.5 mg), hydrochlorothiazide (50 mg), pre-gelatinized starch USP (50 mg), microcrystalline cellulose (100 mg), and magnesium stearate (1 mg). Tablets with, for example, the ethyl ester of (S)-N-[(S)-2-[N$^G$,N$^{G'}$-diethyl-(S)-homoargin-Nα-yl)propionyl]-1,2,3,4-tetrahydroisoquinoline-3-carboxylic acid and hydrochlorothiazide (50 mg) are made by substitution of the former in place of (S)-N-[(S)-2-[N$^G$,N$^{G'}$-diethyl-(S)-homoargin-Nα-yl)propionyl]-1,2,3,4-tetrahydroisoquinoline-3-carboxylic acid in the composition described above.

A combination tablet with a calcium blocker such as nicardipine typically contains (S)-N-[(S)-2-(N$^G$,N$^G$-diethyl-(S)-homargin-Nα-yl)propionyl]-1,2,3,4-tetrahydroisoquinoline-3-carboxylic acid (7.5 mg) nicardipine (15 mg), pre-gelatinized starch USP (50 mg), microcrystalline cellulose (10 mg), and magnesium stearate (1 mg).

EXAMPLE 7

The ACE inhibiting ability of the dipeptides of formula A is assessed in the in vitro model employing a preparation of ACE from crude rabbit lung acetone powder. Hippuryl-histidyl-leucine (HHL) is used as synthetic substrate to be cleaved (hydrolysed) by ACE (D. W. Cushman and H. S. Cheung, Biochem. Pharmacol., 20, 1637 (1971)). The following compounds of formula A, identified by Arabic numerals (referred to above), were assessed for their ability to block the hydrolysis of HHL to the C-terminal dipeptide His-Leu by the ACE preparation. The following table shows this blocking capability expressed as ID$_{50}$ (the dose which causes a 50% inhibition of the hydrolysis where the test compound has been studied at concentrations between $10^{-9}$ to $10^{-4}$M).

| Compound No. | ID$_{50}$(M) |
|---|---|
| (1) | $6 \times 10^{-8}$ |
| (2) | $9 \times 10^{-8}$ |
| (3) | $2.2 \times 10^{-7}$ |
| (4) | $6.5 \times 10^{-8}$ |
| (10) | $1.8 \times 10^{-7}$ |
| (11) | $2.8 \times 10^{-7}$ |
| (12) | $2.3 \times 10^{-7}$ |
| (13) | $6 \times 10^{-8}$ |

(11) N-[2-(N$^G$-methyl-N$^{G'}$-n-butyl-L-homoargin-Nα-yl)propionyl]-L-proline
(12) N-[2-(N$^G$,N$^{G'}$-diethyl-L-homoargin-Nα-yl)butanoyl]-L-proline
(13) N-[2-(N$^G$,N$^{G'}$-diethyl-L-homoargin-Nα-yl)pentanoyl]-L-proline.

I claim:
1. A compound of the formula

$$R^1-CO-CH(R^2)-NH-CH(R^3)-CO-N(R^4)-CH(R^5)-C(O)-R^6 \quad (A)$$

wherein

R$^1$ is hydroxy, lower alkoxy, benzyloxy, amino, (lower alkyl)amino, or di(lower alkyl)amino;

R$^2$ is $$-(CH_2)_n-N(H)-C(=N-R^7)(NHR^8),$$

R$^3$ is hydrogen, lower alkyl, omega-phenyl-lower alkyl, or omega-naphthyl-lower alkyl;

the group $$-N(R^4)-CH(R^5)-C(O)-R^6$$

is an amino acid residue in which the subgroup $$-N(R^4)-CH(R^5)-$$

forms a heterocyclic radical containing one nitrogen atom and up to 9 ring carbon atoms;

R$^6$ is hydroxy, lower alkoxy, benzyloxy, amino, (lower alkyl)amino, or di(lower alkyl)amino;

R$^7$ and R$^8$ are independently lower alkyl or lower alkyl substituted on other than the alpha-carbon with 1 to 5 fluorine atoms; and n is an integer from 3 to 5; or a pharmaceutically acceptable, non-toxic salt thereof.

2. The compound of claim 1 wherein R$^3$ is lower alkyl, benzyl or 2-phenylethyl.

3. The compound according to claim 2 wherein R$^3$ is lower alkyl or 2-phenylethyl; and the group $$-N(R^4)-CH(R^5)-C(O)-R^6$$

is proline (I) or a proline analog in which the pyrrolidine ring is substituted by an oxo group (IV), by hydroxy, mercapto, (lower alkyl)thio, or lower alkoxy (V), or the proline function is replaced with the residues II, III, or VI:

(I), (II), (III), (IV), (V), (VI) structures shown

R$^6$ is hydroxy or benzyloxy; and X is hydrogen, nitro, lower alkyl, chloro or bromo.

4. The compound according to claim 2 wherein R$^3$ is lower alkyl with 1 to 4 carbon atoms.

5. The compound according to claim 4 wherein R$^3$ is methyl, ethyl, or n-propyl.

6. The compound according to claim 3 wherein the group $$-N(R^4)-CH(R^5)-COR^6$$

forms a proline residue.

7. The compound of claim 3 wherein the group $$-N(R^4)-CH(R^5)-COR^6$$

is a residue selected from the groups II, III and VI and R$^6$ is hydroxy.

8. The compound of claim 7 wherein the group $$-N(R^4)-CH(R^5)-COR^6$$

is II.

9. The compound of claim 8 wherein X is hydrogen.

10. The compound of claim 3 wherein R$^7$ and R$^8$ are lower alkyl with 1 to 4 carbon atoms.

11. The compound of claim 10 wherein R$^7$ and R$^8$ are methyl, ethyl, 2,2,2-trifluoroethyl, n-propyl or n-butyl.

12. The compound of claim 11 wherein R$^7$ and R$^8$ are ethyl or 2,2,2-trifluoroethyl.

13. The compound of claim 12 which is (S)-2-[(S)-N-[(S)-1-carboxy-5-N′,N″-diethylguanidinopentyl]alanyl]-1,2,3,4-tetrahydroisoquinoline-3-carboxylic acid or the pharmaceutically acceptable, non-toxic salt thereof.

14. A pharmaceutical composition for the treatment of hypertension in mammals which comprises a pharmaceutically effective amount of a compound of claim 1 and a pharmaceutically acceptable excipient.

15. The composition of claim 14 which further comprises a pharmaceutically effective amount of at least one other antihypertensive.

16. The composition of claim 14 which further comprises a pharmaceutically effective amount of at least one diuretic.

17. The pharmaceutical composition of claim 14 which further comprises a pharmaceutically effective amount of at least one calcium blocker.

18. The composition of claim 14 which further comprises a pharmaceutically effective amount of nicardipine.

19. A method of treating hypertension in mammals which method comprises administering a therapeutically effective amount of a composition of claim 14.

* * * * *